(12) United States Patent
Erbe et al.

(10) Patent No.: US 6,800,245 B1
(45) Date of Patent: Oct. 5, 2004

(54) STERILE POLYMERIZABLE SYSTEMS AND KITS AND METHODS OF THEIR MANUFACTURE AND USE

(75) Inventors: Erik M. Erbe, Berwyn, PA (US); Vasanth Prabhu, Charlestown, PA (US); Jeffrey J Wicklund, Downingtown, PA (US); Anthony M. Wilkes, Limerick, PA (US)

(73) Assignee: Vita Special Purpose Corporation, Wilmington, DE (US)

( * ) Notice: Subject to any disclaimer, the term of this patent is extended or adjusted under 35 U.S.C. 154(b) by 533 days.

(21) Appl. No.: 09/723,445

(22) Filed: Nov. 28, 2000

(51) Int. Cl.$^7$ .............................. A61L 2/04; A61L 2/02; A61L 2/08
(52) U.S. Cl. .............................. 422/1; 422/22; 424/423
(58) Field of Search .............................. 422/1, 22, 34; 424/423; 606/94; 401/176; 604/218

(56) References Cited

U.S. PATENT DOCUMENTS

| | | | |
|---|---|---|---|
| 3,223,083 A | 12/1965 | Cobey | 128/92 |
| 4,341,691 A | 7/1982 | Anuta | 523/116 |
| 4,405,249 A | 9/1983 | Scales | 401/182 |
| 4,515,930 A | 5/1985 | Omura et al. | 526/276 |

(List continued on next page.)

FOREIGN PATENT DOCUMENTS

| | | |
|---|---|---|
| DE | WO 01/24210 A1 | 5/2001 |
| WO | 98/07456 A1 | 2/1998 |

OTHER PUBLICATIONS

Block, Seymour S., editor. Disinfection, Sterilization, and Preservation, 4$^{th}$ ed., 1991, p. 680.*
Allen, D., "Sterilization and medical packaging," *Pharm. & Med. Packaging News*, 1998, http://www.devicelink.com/pmpn/archive/98/04/005.html, 6 pages.
Beagley, K.G., "Package testing: is standardization on the horizon?," *Pharm. & Med. Packaging News*, 1998, http://www.devicelink.com/pmpn/archive/98/03/005.html, 5 pages.

(List continued on next page.)

*Primary Examiner*—Elizabeth McKane
(74) *Attorney, Agent, or Firm*—Woodcock Washburn LLP (57) ABSTRACT

The present invention overcomes the difficulties in the sterilization and delivery of viscous, multi-component compositions that require pre-mixing prior to usage by disclosing a sterile, multi-component, ready-to-use product wherein each component is sterilized independently and then assembled into a sterilized delivery kit. In certain preferred embodiments of the present invention, a sterile, polymerizable system is provided that comprises a plurality of sterile polymerizable monomers, said monomers having been sterilized by passing them through a filter, at least one sterile filler which has been exposed to conditions effective to render said filler sterile, and the sterile monomers and the sterile filler being blended together to form at least one substantially homogeneous blend contained within a sterile delivery vessel. Still other embodiments include a single-use kit that comprises a delivery gun, mix tips, and cartridges that comprise one or more pastes of the present invention that are housed within one or more pouches to ensure sterility of the internal contents.

10 Claims, 1 Drawing Sheet

U.S. PATENT DOCUMENTS

| | | | |
|---|---|---|---|
| 4,973,168 A | 11/1990 | Chan .......................... | 366/139 |
| 5,100,241 A | 3/1992 | Chan .......................... | 366/139 |
| 5,370,221 A | 12/1994 | Magnusson et al. ........ | 206/221 |
| RE35,276 E | 6/1996 | Chan .......................... | 366/139 |
| 5,542,935 A | 8/1996 | Unger et al. ................ | 604/190 |
| 5,681,872 A | 10/1997 | Erbe .......................... | 523/114 |
| 5,735,609 A | 4/1998 | Norton ........................ | 383/33 |
| 5,797,873 A | 8/1998 | Franz et al. ................. | 604/49 |
| 5,814,681 A | 9/1998 | Hino et al. ................. | 523/113 |
| 5,842,786 A | 12/1998 | Solomon ..................... | 366/139 |
| 5,881,536 A | 3/1999 | Müller-Wille et al. ........ | 53/426 |
| 5,902,599 A | 5/1999 | Anseth et al. .............. | 424/426 |
| 5,902,839 A | 5/1999 | Lautenschlager et al. ... | 523/115 |
| 5,914,356 A | 6/1999 | Erbe .......................... | 523/114 |
| 5,997,544 A | 12/1999 | Nies et al. ..................... | 606/92 |
| 6,001,394 A | 12/1999 | Daculsi et al. .............. | 424/489 |
| 6,024,480 A | 2/2000 | Seaton et al. ............... | 366/130 |
| 6,028,242 A | 2/2000 | Tucker et al. ................. | 623/16 |
| 6,056,970 A | 5/2000 | Greenawalt et al. ........ | 424/426 |
| 6,066,325 A | 5/2000 | Wallace et al. ............. | 424/400 |
| 6,075,067 A | 6/2000 | Lidgren ...................... | 523/116 |
| 6,080,801 A | 6/2000 | Draenert et al. ............ | 523/115 |
| 6,103,800 A | 8/2000 | Peterson et al. ............ | 524/296 |
| 6,391,336 B1 * | 5/2002 | Royer ........................ | 424/468 |
| 6,409,972 B1 | 6/2002 | Chan .......................... | 422/131 |

OTHER PUBLICATIONS

"Bioburden testing," *Geneva laboratories, Inc.,* 2000, http://www.genevalabs.com/microtest.html, 3 pages.

"Container and closure integrity testing in lieu of sterility testing as a component of the stability protocol for sterile products," *Guidance for Industry,* Draft, 1998, 1–21.

"Food–preservation," Encyclopaedia Britannica, 2000, http://www.britannica.com/bcom/eb/article/7/0,5716, 120847=18=111121,00.html, 8 pages.

Greenspan, D.C., "Developments in biocompatible glass compositions," *Medical Device & Diagnostic Industry Magazine,* 1999, http://www.devicelink.com/mddi/archive/99/03/011.html, 9 pages.

Hurrell, D.J., "Recent developments in sterilization technology," *Med. Plastics & Biomaterials Magazine,* 1998, http://www.devicelink.com/mpb/archive/98/09/002.html, 12 pages.

Kirk–Othmer, *Concise Encyclopedia of Chemical Technology,* $4^{th}$ Ed., John Wiley & Sons, Inc., 7 pages, prior art.

Millipore–BioPharmaceutical–Liquid, 2000, http://www-.milipore.com/biopharm/products.nsf/docs/4B3LYA, 2 pages.

Sordellini, P.J., et al., "Investigating and preventing BI sterility failures," *Med. Device & Diagnostic Ind. Magazine,* 1996, http://www.devicelink.com/mddi/archive/96/08/012.html, 9 pages.

Sterilization Technologies, 2000, http://www.sterigenics.com/med/stertech/main–stertech.htm, 2 pages.

Types of Heat, 2000, http://www.hsc.wvu.edu/som/micro/MB26PRINT/lecture6/sld009.htm, 6 pages.

Ulatowski, T.A., "Device sterility guidances and validation," *Med. Device & Diagnostic Ind. Magazine,* 1998, http://devicelink.com/mddi/archive/98/06/007.html, 2 pages.

* cited by examiner

*FIG. 1*

STERILE POLYMERIZABLE SYSTEMS AND KITS AND METHODS OF THEIR MANUFACTURE AND USE

FIELD OF THE INVENTION

The present invention relates generally to sterile, polymerizable compositions together with systems, kits, and methods for the sterile manufacture, packaging, and delivery of same. More particularly, the present invention relates to sterile, polymerizable systems and kits that are comprised of pre-mixed, viscous, sterile compositions, especially restorative, and methods of making same.

BACKGROUND OF THE INVENTION

Sterilization is generally defined as rendering a substance incapable of reproduction. In terms of food, medical products or pharmaceuticals, sterilization relates to rending an article free from living microorganisms. The rate of destruction of microorganisms is logarithmic and can be described by the following expression:

$$N_o/N_t = e^{-kt}$$

wherein $N_t$ represents the number of organisms alive at time 't', $N_o$ represents the initial number of organisms, and k equals the kinetic rate constant.

A common manner of expressing sterilization is the sterility assurance level ("SAL"). Because microbiological destruction is logarithmic and expressed in terms of the probability of a survivor, the term "sterile device" does not actually refer to a device that is totally free of viable organisms, but rather to one whose probability of containing a viable organism is so small that it is considered acceptable for a given purpose. Hence, the sterility assurance level (SAL) defines the probability of a viable microorganism being present on an article after sterilization is complete. According to the present FDA regulations, topical medical devices should have a minimum SAL of $10^{-3}$ whereas devices or articles that will directly contact blood or compromised tissues should have a minimum SAL of $10^{-6}$. The integrity of the sterilization method is generally monitored by culturing a test organism. For example, the remaining presence of the highly heat-resistant bacterium, *bacillus subtilis globigii*, can be used as a marker to measure the completeness of sterilization.

There are many different methods of sterilization, each of which presents numerous advantages and disadvantages depending upon the nature of the article or medium to be sterilized. Some of these methods involve the application of heat, pressure, and/or moisture. Moist heat sterilization, i.e., boiling, kills all vegetative cells, most viruses, and fungi within 10 minutes. However, moist heat sterilization is not suitable for many applications in biology and medicine because it causes coagulation of proteins and breakage of hydrogen bonds contained therein.

Another method of sterilization, known as steam sterilization, is the application of steam under pressure within an enclosed chamber known as an autoclave. This method subjects the media to temperatures of typically 121° C. at pressures of 15 pounds per square inch ("psi") above ambient. Autoclave sterilization is capable of killing all microorganisms and their endospores in about 15 minutes. The efficacy of autoclave sterilization is measured by determining the presence or absence of *bacillus stearothermophilus* spores. Media or substances stable in heat may be sterilized at higher temperatures for shorter time periods; conversely, sterilization at lower temperatures require longer sterilization periods.

Dry heat sterilization may involve incineration, i.e., exposing media to high temperatures such as 180° C., or hot-air sterilization, i.e., exposing media to controlled time and temperature conditions. This method is suitable for media such as pharmaceutical products that do not contain water as their primary solvent and cannot be sterilized by other methods. In this instance, dry heat is applied to the media at temperatures of about 100° C. to about 250° C. and exposure times ranging from about one to four hours. The temperature-time relationship is similar to that of steam sterilization.

Sterilization can also occur through the filtration or the physical retardation of microorganisms from a fluid medium by a filter membrane.

Still other methods of sterilization involve the application of radiation, either ionizing or non-ionizing, to sterilize the media. Ionizing radiation involves the application of shorter wavelength radiation, such as gamma rays, beta-rays, x-rays, or high energy electron beams, to ionize the water particles contained within the media to form reactive hydroxyl radicals. This method is commonly used to sterilize pharmaceutical products or disposable dental and medical supplies such as syringes, gloves, or sutures. Activated resins such as those used in bone cements, however, cannot be gamma sterilized because it effects the polymerization process. Non-ionizing radiation involves the application of ultraviolet rays to cause the formation of thymine dimers that inhibit the replication of DNA. Although these rays are non-penetrating to the media, some media can be destroyed in the doses required for effective sterilization.

Another sterilization method is gas sterilization, in which the media is exposed to a vapor or gas such as ethylene oxide ("EtO"). This method is suitable for media, such as foods, pharmaceuticals, and medical equipment, that cannot withstand the temperatures and moisture of steam sterilization or cannot be exposed to radiation. A gaseous sterilant, such as ethylene oxide, is applied under controlled temperature, time, gas concentration, and relative humidity parameters that vary depending upon the nature of the media to be sterilized. Important considerations in the selection of a gas sterilant is the ability of the residue remaining on the media after exposure to the sterilant to volatilize quickly. Because gas sterilization may involve the use of chlorofluorocarbons ("CFC"), plasma gas sterilization, which is a low temperature gas sterilization process involving hydrogen peroxide or other sterilants in the plasma state, is an alternative that is generally safe for the environment. However, plasma technology is currently even more limited than EtO sterilization in terms of what media it can sterilize.

Once an article is sterilized, it needs to be packaged in a manner that will not compromise its sterility until use. Sterilization packaging typically takes place at one location prior to use of the medium, or article, at another location. The main purpose of this packaging is to protect the sterility of the internal contents. Terminal sterilization describes the process of placing an article within its protective container and subsequently sterilizing the container and the article contained therein. On the other hand, aseptic processing involves placing individually sterilized components that have been sterilized by various sterilized methods into a sterilized package that is sealed under sterile conditions. The packaging containers used in these processes are sterilized separately and remain in a sterile environment prior to use. The packaging machinery that is used to fill the packaging containers is also sterilized using steam, sterile gases, or hydrogen peroxide.

Pharmaceutical products are typically rendered sterile by aseptic processing. In aseptic processing, the separate ingredients of a medium, such as a pharmaceutical, are available in sterile form and compounded without microbial contamination. Pharmaceuticals that are injectable may be comprised of aqueous or oily solutions, suspensions or emulsions, and are prepared by conventional manufacturing methods, with special care taken to remove all extraneous particulate matter. Injections must be sterilized by any of the methods given above or terminally sterilized. Some aqueous injectables are not stable and need to be prepared at the time of use by mixing some components prior to use. In this instance, the end user is provided a kit and must assemble the ingredients in a sterile environment immediately prior to injection.

An example of a multi-component system, that must be assembled by the end-user in a sterile environment prior to use, are biocompatible, restorative compositions or biomaterials that are used in orthopaedic and dental applications. Typically, these biomaterials are comprised of a solid component and a liquid component. The solid component may consist of a finely divided polymer of acrylic and/or methacrylic esters and further additives such as polymerization initiators, radiographic contrast agents, and fillers. A typical example of such a powder may consist of small spherical beads (usually about 75 $\mu$m in diameter) of poly (methyl methacrylate) (PMMA) and a small amount of a polymerization initiator such as benzoyl peroxide. The liquid component may consist of an acrylic and/or methacrylic ester monomer and further additives such as polymerization accelerators and stabilizers. A typical example of a liquid is a methyl methacrylate (MMA) monomer, a polymerization activator such as N,N-dimethyl-para-toluidine, and an inhibitor such as hydroquinone. The solid and liquid components are combined immediately prior to use to form a liquid to semisolid paste. The paste may be formed into a desired shape or applied via injection in a wide-mouth syringe or spatula to the implantation site of a prosthesis where it polymerizes.

Presently known products feature deactivated resins which are activated upon combination with other components immediately prior to their delivery or use. These resins and other components are individually wrapped and packaged in an overall aseptic package or kit. An example of such a kit is SIMPLEX® bone cement manufactured by Howmedica of Rutherford, N.J. SIMPLEX® bone cement is comprised of an aseptically packaged ampule of a liquid methyl methacrylate ("MMA") that is combined with an gamma sterilized bag of powder which comprises prepolymerized MMA-styrene and barium sulfate ($BaSO_4$). The end user opens the outer packaging, the ampule, and the bag of powder and combines the liquid and powder components. The user then fills a syringe with the cement in order to deliver the cement to the patient. Some of the disadvantages to this product include product variability; lack of assurance that the components are used in compliance with the manufacturer's instructions; concern over the integrity of the sterilized components; and a shortened time window between preparation of the cement and delivery to the patient. Traditional terminal sterilization is not possible where unpolymerized components must retain activation viability to be delivered to the surgical suite.

There is a need to provide methods for the sterilization and delivery of viscous, multi-component compositions without requiring the end-user to pre-mix or assemble the components. Accordingly, one object of the present invention is to provide a sterile, multi-component, ready to use product that does not require extensive pre-mixing or assembly.

Another object of the present invention is to provide a method for the sterilization of products comprising activated resins or monomers.

Yet another object of the present invention is to provide a method for the sterilization of products comprising heat degradable fillers.

A further object of the present invention is to provide methods for the sterile manufacture and delivery of viscous, multi-component compositions.

An additional object of the present invention is to provide kits comprising the sterile, viscous restorative compositions of the present invention and delivery vessels that allow mixing of these compositions prior to use.

SUMMARY OF THE INVENTION

The present invention overcomes the difficulties in the sterilization and delivery of viscous, multi-component compositions that require pre-mixing prior to usage by disclosing a sterile, multi-component, ready-to-use product wherein each component is sterilized independently and then assembled into a sterilized delivery kit. These systems are suitable for, but not limited to, medical or dental applications that utilize bone cement and restorative compositions. The end products delivered from these kits are sterile upon dispensing. The end user does not need a separate sterile area to pre-mix or assemble the restorative compositions prior to use. The present invention further provides methods for the sterilization of the individual components that comprise the paste compositions that will not adversely alter the characteristics of these components. Moreover, the present invention discloses unique delivery vessels that allow for the premixing of one or more paste compositions prior to and upon delivery of the sterile end product.

The present invention provides one or more viscous, sterile paste compositions, referred to herein as pastes, that are pre-blended and sterile upon delivery to form one or more homogeneous blends. Each sterile, viscous paste is comprised of one or more polymerizable monomers or resin components and one or more fillers. The monomers and fillers are initially and individually sterilized, and then blended together to form one or more sterile viscous pastes. The paste is packaged within a sterile delivery vessel that contains one or more cartridges to house the paste. In multiple paste systems, the pastes are dispensed from their respective cartridges and blended together within the delivery vessel to form at least one viscous, homogeneous blend immediately prior to or upon dispensing.

The polymerizable monomer or resin components that comprise the viscous, paste compositions are preferably ethylenically unsaturated monomers, and more preferably, comprise an acrylate. Examples of such monomers in one such composition include, but are not limited to, bisphenol-A-diglycidyl methacrylate (bis GMA), triethyleneglycol dimethacrylate (TEGDMA), diurethane dimethacrylate (DUDMA), and bisphenol-A-ethyl methacrylate (bis-EMA). In preferred embodiments, the monomers within the paste are activated prior to sterilization. Further additions to the paste may include, but are not limited to, polymerization activators, polymerization initiators, radio pacifiers, reinforcing components (i.e., fibers, particles, micro spheres, flakes, etc.), bioactive fillers, neutralizing resins, diluting resins, antibiotic agents, coloring agents, coupling agents, or radiographic contrast agents. Examples of such additives include, but are not limited to, butylhydroxytoluene (BHT), N,N-dimethyl-p-toluidine (DMEPT), tetraethylene glycol dimethyaniline (TEGDMA), dihydroxyethyl-p-toluidine (DHEPT), UV-9, and benzoyl peroxide (BPO).

The monomers and other additives are combined to form a paste composition precursor which is sterilized prior to adding one or more fillers. The preferred method of sterilization of these monomers and other additives that comprise the paste composition precursor is via high pressure filtration. The monomers, which are preferably activated, are passed through a filter such as a 0.22 µm filter to exclude pathogens. The filtration process is conducted under pressures which range between ambient and 200 psi and more preferably between 2–40 psi. The housing and plumbing fixtures used downstream in the filtration process (including the filter itself) are also sterilized prior to use via steam sterilization (i.e., steam sterilization in place ("SIP") or autoclaving), or similar means, to eliminate or minimize contamination.

In addition to the monomer, the viscous paste or pastes further comprise one or more fillers. These fillers may possess a variety of morphologies such as, but not limited to, needles, particulate, flakes, cylinders, long fibers, whiskers, or spherical particles. In preferred embodiments, the filler is comprised of particles with an average particle size ranging from about less than 1.0 µm up to several millimeters (mm). Preferably, the average particle size distribution ranges from 5 to 20 µm.

The filler may be comprised of an inorganic or organic material. In preferred embodiments, the filler is comprised of an inorganic material. Examples of suitable fillers include, but are not limited to, barium glass, bariumboroaluminosilicate glass, silica, 45S5 glass, bioactive glass, ceramics, glass-ceramics, bioactive synthetic combeite glass-ceramic or combinations thereof. The filler or fillers are generally pre-dried prior to blending with other fillers. In preferred embodiments, one or more fillers are coated with silane prior to sterilization.

The filler may be sterilized by dry heat, E beam, bright light, gamma or EtO methods. The filler is preferably sterilized via dry heat sterilization, i.e., exposed to dry heat at a time and temperature sufficient to render it sterile. If the filler is coated with silane, the sterilization method selected should maintain the integrity of the silane coating. In certain embodiments wherein one or more fillers are coated with silane, the filler is dry heat sterilized with minimal heat penetration to yield a minimally degraded silane surface chemistry. The filler is preferably heated to a temperature of about 140° C. or less for a period of between about 6 hours to about 12 hours, or more preferably, heated to a temperature of about 121° C. for at least 8 hours. In alternative embodiments, the filler can be heated to higher temperatures, such as, but not limited to, temperatures of from about 100° C. to about 250° C. for inversely proportional time periods or shorter periods of time at higher temperatures.

After the filler and the monomer are sterilized, the filler and monomer are combined to form one or more paste compositions. In preferred embodiments, the monomer and filler are combined to form one or more pastes in an aseptic process, i.e., using equipment that has been pre-sterilized and combining the components of the paste in a class 100 or greater clean room. The equipment used to blend the paste or pastes, such as the mixing equipment, spatulas, blades etc., are preferably pre-sterilized using steam or autoclave sterilization.

The paste is preferably contained within a primary packaging which comprises one or more cartridges, caps, O-ring pistons, and external pouches. Each of these components are sterilized prior to the aseptic filling of the paste or pastes. In preferred embodiments, the primary packaging components are sterilized via gamma sterilization.

One or more pastes are aseptically filled into individual cartridges that further comprise a cap and an O-ring piston. The pastes are fed into their respective cartridge barrels using an aseptic filling process as described herein. Air is removed from the cartridge prior to piston insertion. The piston is then assembled into the cartridge to form an air-tight seal. The filled cartridge and piston are then packaged within at least one external pouch. In preferred embodiments, the filled cartridges and piston assemblies are packaged within a dual pouch arrangement, or an inner and outer pouch. The cartridges are then thermally sealed and labeled. The previous steps, of filling the cartridges, assembling the piston into the cartridge, encapsulating the cartridges into one or more pouches and then thermo-sealing the cartridges, are conducted within an isolated system referred to herein as an isolator. The isolator preferably employs vaporous hydrogen peroxide (VHP) to ensure a sterile environment for the preceding process steps.

Further components, that may comprise the delivery system and kit, include a delivery gun and one or more tips, referred to herein as "mix tips", that enable mixing and dispensing of the paste or pastes. Additional components to the systems of the present invention may include a micro delivery system. All of these components are sterile or sterilized and packaged prior to use. In preferred embodiments, these components are sterilized via gamma sterilization. After sterilization is completed, the components are placed with an external package to ensure sterility. An example of this external package may include an oxygen permeable membrane such as a TYVEK®/polyester pouch manufactured by Tolas Healthcare Packaging of Feasterville, Pa. Still other external packages may include, but not be limited to, foil pouches, opaque pouches for light sensitive materials, or other breathable or permeable pouches.

The present invention also discloses methods of preparing a sterile, polymerizable blend. This method comprises the steps of: applying dry heat under time and temperature conditions sufficient to sterilize at least one filler; passing a plurality of polymerizable monomers (or dimers or trimers) through a filter; and combining the monomers and the filler together to form at least one homogeneous blend contained within a first vessel wherein the combined monomers and fillers are dischargeable from a final sterile delivery vessel.

The present invention also discloses sterile, biologically compatible restorative compositions that comprise: a plurality of polymerizable monomers, the monomers having been sterilized by passing them through a filter; at least one filler which has been exposed to conditions of time and temperature effective to render the filler sterile; and the monomers and the filler being blended together to form at least one homogeneous composition contained within a sterile delivery vessel wherein the combined monomers and fillers are dischargeable from the sterile delivery vessel.

Further embodiments disclosed are methods for preparing a sterile, biologically compatible restorative composition. This method comprises the steps of: applying dry heat under time and temperature conditions sufficient to sterilize at least one filler; passing a plurality of polymerizable monomers through a filter, preferably sized to exclude pathogens; and combining the monomers and filler together to form at least one homogeneous composition contained within a sterile delivery vessel. Yet further embodiments of the present invention include sterilization methods for the activated monomer and the silane-coated filler that comprise the paste.

Additional embodiments of the present invention may include shaped bodies made of a sterile polymerizable blend, wherein the blend comprises a plurality of polymerizable monomers, the monomers having been sterilized by passing them through a filter preferably sized to exclude pathogens; at least one filler which has been exposed to conditions of time and temperature effective to render the filler sterile; and the monomers and the filler being blended together to form at least one homogeneous blend contained within a sterile delivery vessel.

Lastly, embodiments of the present invention include methods of restoring tissue in an animal wherein the method comprises the steps of: applying dry heat under time and temperature conditions sufficient to sterilize at least one filler; passing a plurality of polymerizable monomers through a filter sized so as to exclude pathogens; combining the monomers and the filler together to form at least one homogeneous composition contained within a sterile delivery vessel; and applying the composition to an animal whereby the tissue may be restored.

BRIEF DESCRIPTION OF THE DRAWINGS

The foregoing, as well as the following description of certain preferred embodiments, is better understood when read in conjunction with the appended drawings. For the purpose of illustrating the invention, there is shown in the drawings an embodiment that is presently preferred, it being understood, however, that the invention is not limited to the specific methods and apparatuses disclosed.

The present invention overcomes the difficulties in the sterilization and delivery of viscous multi-component compositions that require pre-mixing prior to usage by disclosing a sterile, multi-component, ready-to-use product wherein each component is sterilized independently and then assembled into a sterilized delivery system. These systems are suitable for, but not limited to, medical or dental applications such as viscous, restorative bone cement compositions. The end-products delivered from these kits are considered sterile upon dispensing. The end-user does not need a separate sterile area to pre-mix or assemble the restorative compositions prior to use. The present invention further provides methods for sterilization of the individual components that will not significantly alter the characteristics of these components. Lastly, the present invention discloses a unique delivery system that allows for the pre-mixing of these components prior to, and upon delivery of, the sterile end-product.

The present invention provides one or more viscous, sterile compositions, or pastes, that are pre-blended and sterile upon delivery to form one or more homogeneous blends. Each sterile, viscous paste is comprised of one or more polymerizable monomers and one or more fillers. Further additions to these paste compositions may include, but are not limited to, polymerization activators, polymerization initiators, radio pacifiers, reinforcing components (i.e., fibers, particles, micro spheres, flakes, etc.), bioactive fillers, neutralizing resins, diluting resins, antibiotic agents, or polymerization catalysts. The monomers and the fillers are initially and individually sterilized, and then blended together to form one or more viscous pastes. The paste or pastes are packaged within cartridges and loaded into a sterile delivery vessel. In multiple paste systems, the pastes are dispensed from their respective cartridges and blended together within the delivery vessel to form at least one viscous, homogeneous blend immediately prior to or upon dispensing.

Figure 1:
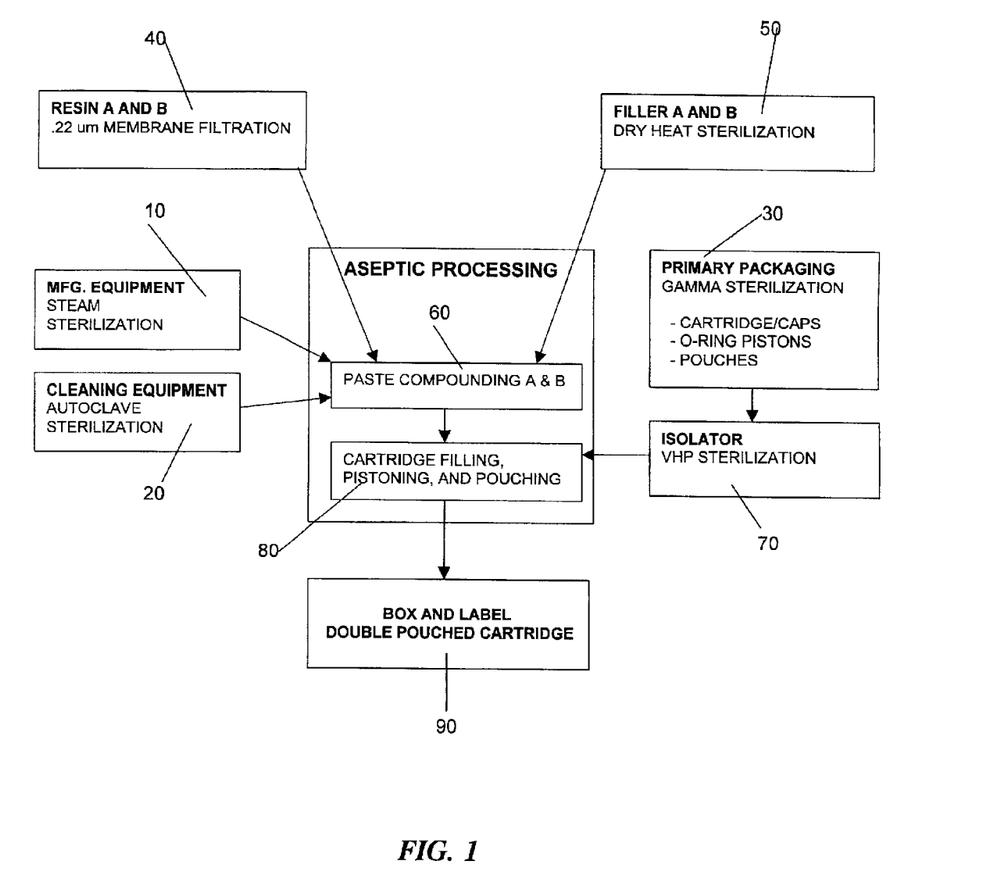
FIG. 1 provides a flow diagram for the steps that comprise the assembly of the sterile, polymerizable paste composition.

FIG. 1 provides a flow diagram of a presently preferred embodiment of the assembly method for the sterile, polymerizable paste composition. Steps 10, 20, and 30 denote the sterilization of the manufacturing equipment, cleaning equipment, and primary packaging, respectively. These steps occur prior to the blending and packaging of the pastes of the present invention. In step 10, the manufacturing equipment, such as the mixing vessel, blades, and other equipment used to blend and contain the paste, is sterilized prior to use, preferably through steam or EtO sterilization. Similarly, in step 20, the cleaning supplies and equipment and processing equipment such as the sterilization filters, housing and plumbing fixtures, and mixing blades, are preferably sterilized via steam sterilization in an autoclave. Lastly, in step 30, the primary packaging for the paste composition, such as the cartridges, caps, O-ring pistons, and pouches, is preferably sterilized via gamma, EtO, electron beam ("E-beam") or other sterilization methods. The selection of the sterilization processes for steps 10, 20, and 30 will vary depending upon the nature of the item to be sterilized. Regardless of the sterilization process, a sterility level of at least about $10^{-6}$, and more preferably at least about $10^{-3}$, is required prior to the use of the equipment in the manufacturing process or prior to contact of the composition precursors or paste prior to packaging.

As mentioned previously, the sterile compositions of the present invention are comprised of one or more polymerizable monomers and one or more fillers. These compositions are referred to herein as pastes to denote that the compositions are viscous liquids. The viscosity of these pastes range from about 40,000 centipoise to about 400,000 centipoise, as measured, for example, by an Brooksfield viscometer.

Relatively low viscosity, syringable pastes are best suited for the filling of bony defects, fracture repair, and implant fixation and revision. Syringable pastes flow to fill voids, and crevices, and adhere tightly to the surface of the bone, tissue, or implant. Flowability can be important for tight adherence and removal of micromotion when implant securing is being achieved. The lack of implant motion can reduce inflammation and determine the success of the implant system over time. Higher viscosity pastes are desirable for larger, load bearing bone defects and easily accessible fracture sites. A "putty" can be manipulated, sculpted and cured in place with immediate high strength capability. Oncological bony defects are well-suited for highly loaded, highly bioactive composites. The use of hand mixed pastes can also facilitate the addition of medicaments, antibiotics, or bone growth factors.

The polymerizable monomer or monomers (or dimers or trimers) that comprise the viscous, paste compositions are preferably ethylenically unsaturated monomers, and more preferably comprise an acrylate functional group. The term "monomers", as used herein, can also represent dimers, trimers, resins, resin components, or any other polymerizable component. Examples of the monomers include, but are not limited to, bisphenol-A-diglycidyl methacrylate (bis GMA), triethyleneglycol dimethacrylate (TEGDMA), or bisphenol-A-ethyl methacrylate (bis-EMA). In preferred embodiments, the monomers within the paste composition are activated prior to sterilization. The monomers may be activated, for example, by the addition of benzoyl peroxide (BPO) or other free radical formers and tertiary amines, or other reducing agents, such as but not limited to DHEPT, DMAPE, DMEPT, ascorbic acid, that may provide an electron withdrawing group that initiates free radical polymerization.

The pastes of the present invention may further comprise, but are not limited to, polymerization inhibitors, polymerization activators, polymerization initiators, radiopacifiers, reinforcing components (i.e., fibers, particles, micro spheres, flakes, etc.), bioactive fillers, neutralizing resins, diluting resins, antibiotic agents, coloring agents, plasticizers, coupling agents, free radical generators, radiographic contrast agents, and antibiotics.

Polymerization inhibitors may be added to the composition to minimize polymerization during storage. Examples of polymerization inhibitors include hydroquinone, and various functional equivalents such as butylhydroxytoluene (BHT), UV-9, methyl ether hydroquinone (MEHQ), 4-benzyloxy phenol and 3,5-diisopropyl phenol.

Polymerization activators are typically amines and are used to promote free radical generation from organic peroxide initiators in addition polymerizations. The free radicals are generated at temperatures around room temperature or below by chemical reduction of the peroxide. Examples of such activators are,N,N-dimethyl-p-toluidine (DMEPT), dihydroxyethyl-p-toluidine (DHEPT), and functional equivalents such as N,N-deimethyl-meta-toluidine, N,N-dimethyl-ortho-toluidine, and N-ethyl-N-hydroxyethyl-meta-toluidine.

Color agents may be added to the composition to impart color and may include dyes, paint pigments, or reduced metal particles.

Plasticizers may be added to the composition to facilitate processing and increase the flexibility of the final product. Examples of plasticizers include TEGDMA, HEMA and phthalates such as diethyl phthalate, benzylbutyl phthalate, dibutyl phthalate, and dibenzyl phthalate.

Coupling agents are used to link the filler within the composition to the polymer matrix. Typical coupling agents include silanes such as γ-methyacryloxypropyltrimethoxysilane or other cationic coupling agents.

Free radical generators are substances within the composition that decompose to form free radicals that begin the process of polymerization in addition reactions. Examples of free radical generators include benzoyl peroxide, tert-butyl peroxide, and diethyl peroxide.

Radiographic or diagnostic contrast agents may be added to the composition to enable the composition to be discerned upon X-ray or other diagnostic means. Examples of such agents include barium boroaluminosilicate glasses and glass-ceramics, barium sulfate ($BaSO_4$), zirconium dioxide ($ZrO_2$), chromium oxide (CrO), Ta, Gd or other heavy metal particulate, or bismuthic compounds such as $Bi_2O_3$ and $Bi(OH)_3$.

In preferred embodiments, the polymerizable systems are comprised of two pastes designated as pastes A and B. In certain preferred embodiments, paste A is comprised of at least one or more fillers and at least one or more resins. Exemplary resin components contained within paste A may include from about 0 to about 25% by weight bispbenol-A glycidyl dimethacrylate (BisGMA), from about 0 to about 18% by weight triethylene glycol dimethacrylate (TEGDMA), from about 0 to about 25% by weight diurethane dimethacrylate (DUDMA), from about 0 to about 2% by weight DHEPT, and from about 0 to about 0.009% by weight butylhydroxytoluene (BHT). In certain preferred embodiments, paste B is also comprised of at least one or more fillers and at least one or more resins. Exemplary resin components contained within paste B may include from about 0 to about 15% by weight bisphenol-A glycidyl dimethacrylate (BisGMA), from about 4 to about 15% by weight triethylene glycol dimethacrylate (TEGDMA), from about 0 to about 25% by weight diurethane dimethacrylate (DUDMA), from about 0–0.07% by weight butylhydroxytoluene (BHT), and from about 0 to about 0.70% by weight of BPO.

Various combinations of the amine:BPO:BHT additives within the paste will yield specific working and set times. Within the composition variables given above, the 2.25:1:0.12 ratio gives the preferred long work time of 5 minutes and the slow set time of 8 to 10 minutes. The more preferred 3 minutes working time and 5 to 7 minutes set time is obtained with a 2.5:1:0.1 amine:BPO:BHT ratio. Each set character will depend on the mass of material used, energy imparted upon mixing, and the temperature of the body (normally 37° C.) at the implant site.

The monomers and other additives are blended together to form one or more paste composition precursors. The duration of the blending operation will vary depending upon the constituents that comprise the paste composition precursors. In preferred embodiments, the blending of the monomers and other additives within the paste composition precursors activates the polymerization of the composition.

Referring again to FIG. 1, step 40 relates to the sterilization of the paste composition precursor. The preferred method of sterilization of the paste composition precursor is via high pressure filtration. In a preferred method, the filter is sized so as to exclude pathogens. The monomers, which are preferably activated during the blending operation, are passed through a filter, such as the 0.22 μm filter manufactured by Millipore, Corporation of Bedford, Mass. The filtration process is conducted under pressures which range between ambient and 200 psi and more preferably between from about 2 to about 40 psi. The housing and plumbing fixtures used downstream in the filtration process (including the filter itself) are also sterilized prior to use via steam sterilization (i.e., steam sterilization in place ("SIP") or autoclaving), or similar means, to eliminate or minimize contamination. The SAL of these paste composition precursors after sterilization is preferably about $10^{-6}$, more preferably about $10^{-3}$. The precursors are processed and stored within a sterile environment, such as a class 100 or greater clean room, to maintain this SAL prior to forming one or more sterile paste compositions.

As mentioned previously, the viscous paste or pastes further comprise one or more fillers. Fillers, which may be inorganic or organic compounds, but preferably are inorganic compounds, are added to the paste to enhance, inter alia, the mechanical or the rheological properties of the paste composition. Examples of suitable fillers include, but are not limited to, barium glass, barium-boroaluminosilicate glass, silica, 45S5 glass, bioactive glass, ceramics, glass-ceramics, bioactive synthetic combeite glass-ceramic or combinations thereof These fillers may possess a variety of morphologies such as, but not limited to, needles, particulate, flakes, cylinders, long fibers, whiskers, or spherical particles. In preferred embodiments, the filler is comprised of particles with an average particle size ranging from less than about 1.0 μm up to a range of from 2 to 3 millimeters (mm). Preferably, the average particle size distribution ranges from 5 to 20 μm.

Optionally, the filler or fillers may be pre-dried and screened prior to sterilization as needed. In preferred embodiments, one or more fillers are coated with silane which acts as a coupling agent prior to sterilization.

In a presently preferred embodiment, paste composition A comprises a silane-coated, glass-ceramic filler that is combined in a blending step with a silane-coated silica to form filler A. An example of a silane-coated, glass-ceramic filler is one manufactured by Mo-Sci, Corp. of Rolla, Mo. and comprised of from 52 to 56% by weight by weight $SiO_2$, from 16 to 25% by weight of CaO, from 12 to 16% by weight of $Al_2O_3$, from 0 to 2% by weight of $Na_2O$, from 0 to 5% by weight of MgO, from 0.05 to 0.4% by weight of $Fe_2O_3$, from 0 to 0.08% by weight of $TiO_2$, and <1% F. The glass filler may, optionally, be pre-dried and screened prior to dry-heat sterilization or, alternatively, gamma-sterilized. Paste composition B comprises a silane-coated barium glass, such as, for example, the barium-boroaluminosilicate glass manufactured by Sci-Pharm, Inc. of Pomona, Calif. and comprised of 52% by weight $SiO_2$, 30% by weight of BaO, 8.5% by weight of $Al_2O_3$, 7.5% by weight of $B_2O_3$ with trace amounts of $Na_2O$, CaO, $Cr_2O_3$, $Fe_2O_3$, and $P_2O_5$. The silane-coated barium glass is further combined with a silane-coated, synthetic Combeite glass-ceramic and a silane-coated silica in a blending step to form filler B.

In preferred embodiments, the filler level of pastes A and B can vary from 65 to 85% by weight total filler content with the preferred bioactive glass-ceramic, such as the Combeite glass-ceramic("CGC") filler and composition disclosed in U.S. Pat. No. 5,681,872, and assigned to Orthovita, Inc., the assignee of the present invention which is incorporated herein in its entirety by reference. The content of the preferred bioactive glass-ceramic preferably ranges from about 10 to about 99% by weight of that filler. It is preferred that the particle size distribution of the fillers be broad, bimodal, or preferably trimodal, also of which being less than about ~300 micrometers, even more preferably less than 50 $\mu$m, with less than about 5% by weight being sub 0.1 microns in size.

Referring again to FIG. 1, step 50 discloses one embodiment of the sterilization of the fillers prior to combining with the paste composition precursors. Methods for sterilizing the fillers may include dry heat, gamma, E beam, bright light or EtO. If the filler is coated with silane, the sterilization method selected should maintain the integrity of the silane coating.

In step 50, the filler or fillers are preferably sterilized via dry heat sterilization or exposed to dry heat at a time and temperature sufficient to render the filler sterile. The filler is typically heated to a temperature of about 140° C. or less for a period of between about 6 to about 12 hours, or more preferably, heated to a temperature of about 121° C. or less for at least 8 hours. In alternative embodiments, the filler can be heated to higher temperatures, such as, but not limited to, temperatures of from about 100° C. to about 250° C. for inversely proportional time periods or shorter periods of time at higher temperatures. Process variables that effect the length of time and temperature that the filler is sterilized at are the volume of filler, the loading of the filler within the oven or kiln, the ramp rate of the oven or kiln, the dwell time, and atmosphere in the dry heat operation. In embodiments wherein one or more fillers are coated with silane, the filler is distributed in a thin layer on a fluidized bed, such as a rotary kiln, to allow sufficient heat penetration of the filler without degrading the silane coating. The SAL of the filler after sterilization is about $10^{-6}$, or more preferably about $10^{-3}$. The filler is maintained within a sterile environment, such as a class 100 or greater clean room, to ensure its SAL prior to combining with the paste composition precursor.

After the filler and monomer are sterilized, the filler and the monomer are combined to form one or more paste compositions. In preferred embodiments such as the process disclosed in step 60 of FIG. 1, the paste composition precursor comprising the monomer and filler are combined to form one or more pastes in an aseptic process, i.e., using equipment that has been pre-sterilized and combining the components of the paste compositions in a class 100 or greater clean room. Depending upon the components of the paste composition, a vacuum that ranges from 0 to 29.5 in Hg may be pulled to prevent auto polymerization during compounding and/or to minimize macro-sized air bubbles. For example, in certain presently preferred embodiments, the A paste composition that will fill the A-side cartridge has an applied vacuum of 20 in Hg pulled whereas the B paste composition that will fill the B-side cartridge has an applied vacuum of 5 in Hg. The equipment used to blend the monomer, filler, or other constituents to form the paste compositions, such as the mixing equipment, spatulas, blades etc., are preferably pre-sterilized using steam (referring to step 10) or autoclave sterilization (referring to step 20).

The paste is preferably contained within a primary packaging that comprises one or more cartridges, caps, O-ring pistons, and external pouches. Each of the primary packaging components are sterilized prior to the aseptic filling of the paste or pastes (see step 30 of FIG. 1). In preferred embodiments, the primary packaging components are sterilized via gamma sterilization or other sterilization techniques such as EtO, or E-beam sterilization (see step 30 of FIG. 1).

Referring to step 70 of FIG. 1, one or more pastes are aseptically filled into cartridges that further comprise a cap and an O-ring piston. In preferred embodiments, paste compositions A and B are loaded into the a monolithic, double-chambered cartridge such as the double-chambered cartridge that is manufactured by Mixpac Systems AG of Rothreuz, Switzerland. Preferably, the double-chambered cartridge has two chambers that keep the pastes separated from each other. Further embodiments of the present invention may include, but are not limited to, multiple-chambered, i.e., triple- or quadruple-chambered cartridges for three or four paste compositions. The cartridge preferably has a dispensing nozzle and cap to seal the contents prior to use.

Referring to FIG. 1, step 80, or the steps, of filling the cartridges, assembling the piston into the cartridge, encapsulating the cartridges into one or more pouches and then thermo-sealing the cartridges, is conducted within an isolated system or isolator (see step 70). The isolator preferably employs vaporous hydrogen peroxide (VHP) to obtain a sterile environment or SAL of from about $10^{-6}$ to about $10^{-5}$. However, other methods of rendering the area sterile may be used without departing from the spirit of the invention. Air is removed from the cartridge prior to the filling process and platen insertion. A platen is then inserted into each individual chamber of the cartridge. The paste is aseptically filled into the cartridge using filling equipment which is selected to minimize the risk of contamination of the sterile material. Preferably, non-product contact filling equipment such as the Trideck filler manufactured by Trideck, Inc. of Brookfield, Conn. is used. Depending upon the composition of the paste or pastes, the filling may further be conducted under hot or cold temperatures (hot filled or cold filled) or conducted under vacuum. After the cartridge or chambers of the cartridge are filled, the O-ring piston assembly is assembled into the cartridge to form an air-tight seal. The filled cartridge and piston may then be packaged within an external pouch. In preferred embodiments, the filled cartridges and piston assemblies are packaged within a dual pouch arrangement, or an inner and outer pouch.

Examples of the external packaging for the filled cartridges my comprise a TYVEK®/polyester pouch manufactured by Tolas Healthcare Packaging of Feasterville, Pa. and/or polyvinyl pouch. Still other external packages may include, but not be limited to, foil pouches, opaque pouches for light sensitive materials, or other permeable pouches. The cartridges are then thermally sealed. In certain preferred embodiments, the cartridge is inserted into an internal polyvinyl pouch which is then placed within a TYVEK®/polyester pouch. Both internal and external packages are thermally sealed simultaneously.

Referring to FIG. 1, step 90 occurs when the packaged cartridge is labeled and placed in stock in an environment that maintains the integrity and sterility of the paste or pastes contained therein. The filled cartridges are then inspected for sterility and other parameters such as, but not limited to, pouch seal integrity dye test, pouch test integrity pull test, composite set time, polymerization stability, prior to release. In preferred embodiments, the sterility may be tested on each production lot of pastes or other components of the system in accordance with the procedures provided in the following test references: Test Procedure PSI SOP LP074 (Bacterial Endotoxin Inhibition/Enhancement Test), Test Procedure PSI SOP LP012 (Bacterial Endotoxin Limit Test) found in the FDA *Guidelines on Validation of the Limulus Amebocyte Lystate Test as an End-Product Endotoxin Test for Human and Animal Parenteral Drugs, Biological Products, and Medical Devices* (FDA, December 1987) and *Bacterial Endotoxins Test*, Chap. 85 of the *United States Pharmacopeia* 24. Further tests may include the Biological Indicator Sterility Test provided in *U.S. Pharmacopeial Guidelines for Biological Indicators* and ANSI/AAMI ST-34: 1991. The sterility levels of the system components such as the paste or pastes, inner pouch, cartridges, and fillers are preferably tested on a lot-by-lot basis to subscribe to or exceed the FDA sterility guidelines.

The filled cartridges may be packaged along with accessories for the presently preferred embodiment of the present invention. These accessories are individually sterilized and packaged into a single-use kit. This kit may comprise a delivery gun and one or more tips, or "mix tips" of various sizes and configurations. In preferred embodiments, a single-use delivery gun, such as the gun manufactured by Mixpac Systems AG of Rothreuz, Switzerland, may be used that accommodates a dual-chambered cartridge that contains two different paste compositions. Still further accessories to the kit of the present invention includes the straight and tapered mix tip of the present invention. In preferred embodiments, these mix tips are also manufactured by Mixpac Systems AG of Rothreuz, Switzerland, and are sized to fit the nozzle end of the cartridge. The mix tip has mixing elements contained therein that allow the paste compositions in the separate chambers to mix and delivery a substantially homogeneous blend. Other components to the systems of the present invention may include a micro delivery system. All of the components are pre-sterilized and packaged prior to use. In preferred embodiments, the components are sterilized via gamma sterilization. After the components are sterilized, the components are placed into an external package to ensure sterility. An example of this external package may include a TYVEK®/polyester pouch manufactured by Tolas Healthcare Packaging of Feasterville, Pa. The present invention may further include additional kits that comprise refills of the paste compositions, preferably in cartridge form, and mix tips.

In certain preferred embodiments, the end-user opens the external and internal pouches that house the dual-chambered cartridge and loads the cartridge into the delivery gun within a sterile environment, such as a surgical operating room. The plunger of the gun uniformly engages the platens within each chamber to dispense the pastes. The individual caps covering the outlets on each chamber of the cartridge are removed and the mix tip is installed. The mix tip is preferably shaped to allow the pastes to flow through their respective outlets on each chamber and ultimately to flow through one central orifice into a mixing element. The mix tip further has an mixing element that is shaped like an auger to combine the pastes into a homogeneous blend prior to dispensing. For best results, the first inch of the blend is discarded to ensure uniform mixing of both pastes. Depending upon the composition of the pastes, the blended, restorative composition should be used approximately 5–8 minutes after dispensing.

By way of example, three sterile polymerizable systems were made from three different production lots in accordance with the methods of the present invention. These systems were comprised of two pastes designated A and B, both of which were comprised of at least one sterile filler and at least one sterile polymerizable monomer. The pastes were filled into separate chambers of a dual chambered cartridge as disclosed herein and packaged within an internal and external pouch that was sealed simultaneously. Each system was subjected to the following tests: bacterial endotoxin inhibition/enhancement tests and bacterial endotoxin limit tests. These tests were performed in accordance with following FDA Guideline—*Validation of Limulus Amebocyte Lysate as an End-Product Endotoxin Test for Human and Parenteral Drugs, Biological Products, and Medical Devices* ("LAL"). These tests showed that the paste compositions were compliant with or exceeded FDA Guidelines. Further testing and analysis was performed for the following: endotoxin tests on the paste compositions; product sterility testing on the paste compositions; product sterility testing on swabs of the outside of the inner pouch to insure that the inner pouch is sterile; and product sterility testing on swabs of the outside of the cartridges; biological indicator sterility test certificate for the filler comprised within the paste compositions. All of these tests showed that the systems met or exceeded FDA and/or ASTM guidelines.

The present invention also discloses methods of preparing sterile, polymerizable blends. This method comprises the steps of: applying dry heat under time and temperature conditions sufficient to sterilize at least one filler; passing a plurality of polymerizable monomers through a filter; and combining the monomers and the filler together to form at least one homogeneous blend contained within a sterile delivery vessel wherein the combined monomers and fillers are dischargeable from the sterile delivery vessel.

The present invention also discloses sterile, biologically compatible restorative compositions that comprise: a plurality of polymerizable monomers, the monomers having been sterilized by passing them through a filter; at least one filler which has been exposed to conditions of time and temperature effective to render the filler sterile; and the monomers and the filler being blended together to form at least one homogeneous composition contained within a sterile delivery vessel wherein the combined monomers and fillers are dischargeable from the sterile delivery vessel.

Further embodiments disclosed are methods for preparing a sterile, biologically compatible restorative composition. This method comprises the steps of: applying dry heat under time and temperature conditions sufficient to sterilize at least one filler, passing a plurality of polymerizable monomers through a filter; and combining the monomers and filler together to form at least one homogeneous composition contained within a sterile delivery vessel. Yet further embodiments of the present invention include sterilization methods for the activated monomer and the silane-coated filler that comprise the paste.

Additional embodiments of the present invention may include shaped bodies made of a sterile polymerizable blend, wherein the blend comprises a plurality of polymerizable monomers, the monomers having been sterilized by passing them through a filter; at least one filler which has been exposed to conditions of time and temperature effective to render the filler sterile; and the monomers and the filler being blended together to form at least one homogeneous blend contained within a sterile delivery vessel.

Lastly, embodiments of the present invention include methods of restoring tissue in an animal wherein the method comprises the steps of: applying dry heat under time and temperature conditions sufficient to sterilize at least one filler, passing a plurality of polymerizable monomers through a filter; combining the monomers and the filler together to form at least one homogeneous composition contained within a sterile delivery vessel; and applying the composition to an animal whereby the tissue may be restored.

Thus, there had been described presently preferred embodiments of a sterile, polymerizable kit and/or system and methods for the manufacture and use thereof that are comprised of one or more sterile compositions and a delivery system or kit. Although the present invention has been described with reference to restorative biomaterials, it should be understood that aspects of the present invention, such as the sterile compositions themselves, the sterilization methods of the constituents that comprise the compositions, and their methods of use for a restorative bone composition, are not limited to the particular embodiments disclosed. While the present invention has been particularly shown and described with reference to the presently preferred embodiments thereof, it is understood that the invention is not limited to the embodiments specifically disclosed herein. Numerous changes and modifications may be made to the preferred embodiment of the invention, and such changes and modifications may be made without departing from the spirit of the invention. It is therefore intended that the appended claims cover all such equivalent variations as they fall within the true spirit and scope of the invention.

We claim:

1. A method of preparing a sterile, polymerizable blend, the method comprising the steps of:
   sterilizing at least one filler with a coupling agent, via dry heat sterilization under conditions sufficient to maintain the integrity of said coupling agent;
   sterilizing a plurality of polymerizable monomers via high pressure filtration; and
   combining said monomers and filler together aseptically to form at least one homogeneous blend contained within a sterile delivery vessel from which the combined monomers and filler can be discharged.

2. The method of claim 1 wherein said coupling agent is silane.

3. The method of claim 1 wherein the filler is sterilized at a temperature of about 121° C. for at least 8 hours.

4. The method of claim 1 wherein the filler is sterilized at a temperature of about 140° C. for at least 6 hours.

5. The method of claim 1 wherein the delivery vessel comprises one or more sterile cartridges, one or more sterile pistons, and one or more sterile caps.

6. The method of claim 1 wherein the delivery vessel is sterilized by gamma radiation.

7. The method of claim 1 wherein the delivery vessel is sterilized in an autoclave.

8. The method of claim 7 wherein the delivery vessel is sterilized in an autoclave at about 121° C. for at least 30 minutes.

9. A method of preparing a sterile, biologically compatible restorative composition, the method comprising the steps of:
   applying to at least one filler with a coupling agent, dry heat under time and temperature conditions sufficient to sterilize said at least one filler with a coupling agent while maintaining the integrity of said coupling agent;
   applying high pressure filtration sufficient to sterilize a plurality of polymerizable monomers; and
   combining said monomers and filler together aseptically to form at least one homogeneous composition contained within a sterile delivery vessel.

10. A method of restoring tissue in an animal, the method comprising:
   applying to the animal a sterile restorative compositions from a sterile delivery vessel;
   the composition being formed by applying dry heat under time and temperature conditions sufficient to sterilize at least one filler with a coupling agent and applying dry heat under conditions sufficient to maintain the integrity of said coupling agent;
   applying high pressure filtration sufficient to sterilize a plurality of polymerizable monomers;
   combining said monomers and filler together aseptically to form at least one homogeneous composition contained within a sterile delivery vessel; and
   applying said composition to said animal whereby the tissue may be restored.

* * * * *

UNITED STATES PATENT AND TRADEMARK OFFICE
CERTIFICATE OF CORRECTION

PATENT NO. : 6,800,245 B1
DATED : October 5, 2004
INVENTOR(S) : Erbe et al.

It is certified that error appears in the above-identified patent and that said Letters Patent is hereby corrected as shown below:

Column 3,
Line 46, please delete "an" and insert -- a -- therefor.

Column 8,
Line 34, please delete "an" and insert -- a -- therefor.

Column 9,
Line 20, please delete "are,N,N-dimethyl" and insert -- are ,N,N-dimethyl -- therefor.
Line 22, please delete "deimethyl" and insert -- dimethyl -- therefor.
Line 57, please delete "bispbenol-A" and insert -- bisphenol-A -- therefor.

Column 10,
Line 4, please delete "0-0.07%" and insert -- 0-.07% -- therefor.
Line 54, after "thereof" insert -- . -- therefor.

Column 11,
Line 4, please delete "by weight" (second occurrence) therefor.
Line 42, please delete "beat" and insert -- heat -- therefor.

Column 12,
Line 31, after "the" please delete "a" therefor.

Column 13,
Line 2, please delete "my" and insert -- may -- therefor.

UNITED STATES PATENT AND TRADEMARK OFFICE
CERTIFICATE OF CORRECTION

PATENT NO.    : 6,800,245 B1
DATED         : October 5, 2004
INVENTOR(S)   : Erbe et al.

It is certified that error appears in the above-identified patent and that said Letters Patent is hereby corrected as shown below:

Column 14,
Line 10, please delete "an mixing" and insert -- a mixing -- therefor.

Signed and Sealed this

Twenty-ninth Day of November, 2005

JON W. DUDAS
*Director of the United States Patent and Trademark Office*